United States Patent [19]

Newkirk et al.

[11] 4,241,224
[45] Dec. 23, 1980

[54] FIBER LUBRICANTS DERIVED FROM THE OXYALKYLATION OF A GLYCEROL-1,3-DIALKYLETHER

[75] Inventors: David D. Newkirk; Robert B. Login, both of Woodhaven, Mich.

[73] Assignee: BASF Wyandotte Corporation, Wyandotte, Mich.

[21] Appl. No.: 82,792

[22] Filed: Oct. 9, 1979

Related U.S. Application Data

[62] Division of Ser. No. 956,052, Oct. 30, 1978.

[51] Int. Cl.$^3$ .............................................. C07C 43/11
[52] U.S. Cl. ...................................... 568/619; 568/620
[58] Field of Search ................... 568/619, 620; 428/395

[56] References Cited

U.S. PATENT DOCUMENTS

| | | | |
|---|---|---|---|
| 2,425,755 | 8/1947 | Roberts et al. | 568/620 |
| 2,932,616 | 4/1960 | Blake | 568/620 |
| 2,932,670 | 4/1960 | Blake | 568/620 |
| 3,925,588 | 12/1975 | Marshall et al. | 568/620 |

FOREIGN PATENT DOCUMENTS

2516736  4/1975  Fed. Rep. of Germany ........... 568/620

*Primary Examiner*—Werren B. Lone
*Attorney, Agent, or Firm*—Andrew E. Pierce

[57] ABSTRACT

Lubricants and processing aids for synthetic fibers, particularly polyester and nylon fibers, are disclosed comprising compounds having the structural formulas:

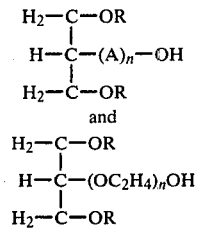

and in which R is an aliphatic group generally having about 3 to about 22 carbon atoms; A is a mixture of residues from ethylene oxide and at least one other lower alkylene oxide, preferably a heteric mixture of oxyethylene and oxypropylene residues in the respective ratio by weight of 20:80 to 90:10; and n has a value to produce a molecular weight of about 300 to about 3000.

Where liquid products are desired which contain the higher numbered carbon chain residues, low viscosity compounds can be obtained by oxyalkylating a glycerol-1,3-dialkylether with a mixture of ethylene oxide and 1,2-propylene oxide in the respective ratio as set forth above. Thus it is possible by properly balancing the carbon chain length of the R groups in the lubricant compounds of the invention with the oxyalkylene chain length to obtain products varying between water insoluble and water soluble. The oxyalkylated fiber lubricants of the invention have the properties of viscous liquids, solids or pastes at ambient temperature.

2 Claims, No Drawings

FIBER LUBRICANTS DERIVED FROM THE OXYALKYLATION OF A GLYCEROL-1,3-DIALKYLETHER

This is a division, of application Ser. No. 956,052, filed Oct. 30, 1978.

BACKGROUND OF THE INVENTION

1. Field of the Invention

This invention relates to the false twist processing of multi-filament and mono-filament synthetic fibers, particularly polyester and nylon fibers with fiber processing aids applied as spin-finishes subsequent to extrusion of the fibers from the spinneret.

2. Description of the Prior Art

In the production of polyester and polyamide filament, the addition of a chemical coating after extrusion from the spinneret is essential in order to process the emerging filaments into fibers. It is known to utilize polyoxyethylene compounds as fiber lubricants as well as heteric polyoxyalkylenes derived from the random or heteric polymerization of ethylene oxide and 1,2-propylene oxide utilizing fatty acid and fatty alcohol initiators. The fatty acid or fatty alcohol residues provide lubricity and the polyoxyalkylene residues provide surface wetting and impart water solubility to the lubricating compound.

In accordance with U.S. Pat. Nos. 2,457,139 and 2,425,755, it is known to obtain oxyalkylated compound lubricants utilizing diols, monols, and fatty acids as polymerization initiators. Both U.S. Pat. No. 3,925,588 and German Offen No. 2,516,736 disclose the heteric oxyalkylation of a mixture of ethylene oxide and 1,2-propylene oxide with higher fatty acids such as stearic acid in the production of lubricants particularly useful in treating multi-filament polyester yarn. The heteric oxyalkylated polymer structure is known to provide liquid products at ambient temperature as opposed to similar compositions obtained by oxyethylating. In U.S. Pat. No. 2,932,670 there is disclosed the ethoxylation of glycerol-1,3-dialkylethers wherein the alkyl radical can contain from 6 to 16 carbon atoms. Such compounds are disclosed as being useful as wetting agents and detergents. The glycerol-1,3-dialkylether intermediates used in the preparation of the fiber lubricants of this invention and methods for their preparation are disclosed in Kogyo Kagaku Zasshi No. 64 (11), 1958–1964.

SUMMARY OF THE INVENTION

It is a primary object of this invention to provide fiber lubricating compounds or processing aids useful as a coating on synthetic fibers such as polyester or nylon fibers. The compounds have a balanced blend of lubricity in combination with the properties of water-dispersibility or water-solubility. Said compounds can be low viscosity liquids at room temperature, if desired. Thus certain lubricant compounds of the invention can be applied to the fiber, if desired, without dilution in water since certain embodiments of the lubricants of the invention have low viscosities at ambient temperature as compared to certain lubricant compounds of the prior art. In addition, certain of the lubricant compounds of the invention exhibit the characteristic of self emulsification and others exhibit the characteristic of water solubility at ambient temperatures thus allowing application of these lubricants to textile fibers by utilizing aqueous dispersions, emulsions or solutions of the lubricant compounds.

These and other objects are accomplished in accordance with this invention by utilizing lubricant compounds derived from an intermediate compound obtained by the reaction of an epihalohydrin, preferably epichlorohydrin, with a fatty alcohol. Such intermediates have the structural formula:

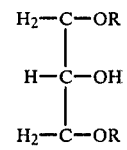

wherein R is derived from the residue of a straight or branched chain aliphatic alcohol. The hydroxyl group in the center of the molecule is reactive in an oxyalkylation reaction. Upon oxyalkylation of this intermediate with either (1) ethylene oxide or (2) a mixture of ethylene oxide and at least one other lower alkylene oxide, preferably 1,2-propylene oxide, so as to obtain a polyoxyalkylated chain containing heteric or random groups of the residues thereof, the following compounds are obtained:

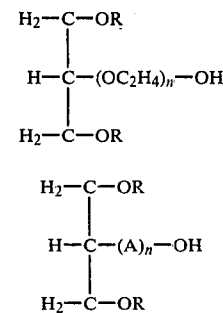

wherein R is a straight or branched chain aliphatic radical generally having about 3 to about 22 carbon atoms; A is preferably a mixture of oxyethylene and oxypropylene residues in the respective ratio by weight of 20:80 to 90:10; and n has a value to produce a molecular weight of about 300 to about 3000.

The lubricant compositions of the invention provide an improved balance of lubricity and wetting ability derived from the fact that the hydrophile oxyalkylene groups are attached to the center of the hydrophobic portion of the lubricant molecule.

DETAILED DESCRIPTION OF THE INVENTION AND OF THE PREFERRED EMBODIMENTS

The lubricant compounds of the invention provide a novel biodegradable fiber lubricant which overcomes certain of the difficulties generally associated with textile fiber lubricants. For instance, where mineral oil or a fatty acid ester such as butyl stearate is utilized in combination with other components as a fiber lubricant, such compositions are difficult to apply to the fiber since the compositions require the use of an emulsifier such as a nonionic or anionic emulsifier and there is a tendency toward nonuniformity of the application of the fiber lubricant to the fiber under these circumstances. In addition, such compositions utilizing mineral oil or fatty acids esters are not easily biodegraded and thus represent a pollution problem in the sense that an oil film or sludge is discharged into surrounding rivers and waterways adjacent to the textile factory where such lubricants are utilized.

Where the fiber lubricant contains a polyoxyalkylated fatty alcohol or fatty acid, it is possible to provide self-emulsifying or water-soluble lubricating compositions so that the appearance of rivers or surrounding waterways contaminated with such compounds is not seriously affected. Nevertheless these compounds are not readily subject to biodegradation, a general characteristic of compounds which include a polyoxyalkylene chain in the molecule.

The compounds of the invention while containing polyoxyalkylene chains in the molecule are unique in that the polyoxyalkylene chains are attached to the hydrophobe in the center thereof providing a more readily biodegradable fiber lubricating compound which can be attacked by bacteria on either end of the chain of the hydrophobe thus eventually breaking up the polymer into smaller components which can be more readily biodegraded.

Another drawback of certain of the prior art lubricants is that it is difficult to incorporate the higher fatty acid or alcohols in the fiber lubricant compound and yet obtain compounds having low viscosity which will permit ease of application to the textile fiber as well as an improved lubricating effect. The compounds of the invention overcome this disadvantage since compounds of the invention can be oxyalkylated with a relatively small amount of ethylene oxide in comparison with the relatively long chains on the hydrophobe thus maintaining the viscosity of the lubricant compound either as a liquid at ambient temperature or as a paste. Alternatively, where the lubricant compound of the invention is oxyalkylated utilizing, for instance, a mixture of ethylene oxide and 1,2-propylene oxide similarly long carbon chains can be utilized as the hydrophobe together with a relatively long oxyalkylene chain. The preferred mixture of ethylene oxide and 1,2-propylene oxide is employed in a ratio so as to maintain a suitable balance in the compound between the desired water-solubility or self-emulsification characteristics and low viscosity at ambient temperature.

The fiber lubricants of the invention are prepared by the ethoxylation or mixed oxyalkylation of an intermediate compound which is obtained by reacting an epihalohydrin, preferably epichlorohydrin, with a straight or branched-chain fatty alcohol. Useful mixed alkylene oxides which can be employed in the preparation of the oxyalkylene copolymer fiber lubricants of the invention are mixtures of ethylene oxide and another lower alkylene oxide. Generally, 1,2-propylene oxide, butylene oxide, and hexylene oxide can be employed in admixture with ethylene oxide in the preparation of said fiber lubricants. Both block and heteric copolymers are useful but, preferably, the fiber lubricants of the invention are derived from the reaction of mixtures of ethylene oxide and 1,2-propylene oxide. The intermediate obtained is a diether containing a single hydroxyl group located in the center of the molecule. The glycerol-1,3-dialkylether intermediate can be prepared by reacting epichlorohydrin with a straight chain or branched chain aliphatic alcohol in the presence of an alkali metal, for instance sodium. Best results are obtained by the addition of the epichlorohydrin dropwise to a large excess of alcohol containing a slight molar excess of alkali metal based upon the epichlorohydrin. The rate of addition is such as to control the exotherm of the reaction at a temperature such that a minimal quantity of tarry products are obtained.

Alternatively, said intermediate compound can be formed by reacting epichlorohydrin with straight chain or branched alcohol catalyzed with $BF_3$ etherate or similar Lewis acid. Upon base treatment, the alkoxy glycidyl ether is formed which can then be added to a large excess of alcohol catalyzed with $BF_3$ etherate or similar Lewis acid to obtain the product. By using a different alcohol in the first and third step, a mixed glycerol-1,3-dialkylether intermediate can be prepared. Both of these preparations, base catalyzed and Lewis acid catalyzed, yield some tetraether which can be removed by distilling off the glycerol-1,3-dialkylether intermediate or can be left mixed with the intermediate for conversion to the fiber lubricants of this invention.

Representative useful straight chain or branched chain fatty alcohols generally contain about 3 to about 22 carbon atoms, preferably about 10 to about 22 carbon atoms, and most preferably about 12 to about 22 carbon atoms in the chain and are as follows: butyl, pentyl, hexyl, heptyl alcohols, octyl alcohol, methylisobutyl carbinol, decyl alcohol, cetyl alcohol, 2-ethylhexyl alcohol, dodecyl alcohol, and stearyl alcohol. The fatty alcohols are available commercially as mixtures of fatty alcohols such as mixtures of fatty alcohols having carbon chain lengths ranging between about 12 and about 15, as represented by the commercially available products sold under the trademark "NEODOL 25" or the fatty alcohol blend sold under the trademark "EPAL 12/85" which is a mixture of fatty alcohols in which the fatty alcohol having a 12 carbon chain predominates to the extent of 85 percent. While epichlorohydrin is the preferred reactant for the production of the glycerol-1,3-dialkylethers other epihalohydrins can be utilized such as the bromo and fluoro epihalohydrins.

In general the fiber lubricants of the invention exhibit a desirable balance of properties including biodegradability and self-emulsifiability in water together with low viscosity at ambient temperature. The oxyalkylated fiber lubricant products of the invention are generally fluids at ambient temperature. Because the fiber lubricants of the invention can be easily prepared so as to contain two fatty alcohol chain residues instead of one as in the prior art fiber lubricants of the invention prepared by the ethoxylation or alkoxylation of fatty alcohols or fatty acids, the fiber lubricants of the invention exhibit excellent lubricity characteristics while at the same time retaining the characteristics of fluidity at ambient temperature and being either self-emulsifiable or water-soluble.

The low viscosity of the fiber lubricants of the invention make it possible to apply them to the fibers without dilution by passing the fibers through a trough or having the fibers make contact with a "kiss" roll rotating in a trough in which the fiber lubriants are contained. The fiber lubricants of the invention can also be similarly applied to the fibers after dilution with water. Generally, about 0.1 percent by weight to about 1.5 percent by weight, preferably about 0.1 percent to about 1 percent by weight, of the fiber lubricants of the invention, based upon the weight of the fibers, are applied to thermoplastic synthetic fibers to improve the lubricity thereof.

The water-solubility or water-dispersibility of the fiber lubricants of the invention facilitates the subsequent scouring operation utilized to remove the lubricant subsequent to the mechanical and heat treatment of the yarn prior to the dyeing operation. In addition the water-solubility or self-emulsifiability of the fiber lubricants of the invention aid in disposal of these materials by the textile mill usually preventing the accumulation of an oil film or slick in nearby streams or ponds as would be the case with a mineral oil-based fiber lubricant of the prior art. While the mineral oil type fiber lubricants would be very slowly decomposed by bacteria subsequent to disposal, the nature of the fiber lubricants of the invention permit biodegradation to take place readily.

The fiber lubricants of the invention have excellent stability to smoking under conditions of use at elevated temperature in the mechanical and heat treatment operation subsequent to extrusion of the fiber, as compared to prior art ethoxylated and alkoxylated fatty acids and fatty alcohols as well as mineral oils utilized in the prior art. Additional high temperature stability of the fiber lubricants can be obtained by the addition of conventional stabilizers and anti-oxidants as is known in the art.

The following test methods were used in evaluating the suitability as fiber lubricants of the compounds of the instant invention.

The thin film smoke point of fiber lubricants of the invention was evaluated by inserting about 0.5 gram of lubricant into a machined depression (so as to fill the depression) on one face of a stainless steel cylinder measuring 1 inch by 2⅜ inches in diameter. The cylinder has a drilled opening on its side into which about one inch of the bulb end of a glass laboratory thermometer is inserted in order to determine the temperature of the cylinder. The machined depression on one face of the cylinder is 1/16 inch deep and extends over the whole face of the cylinder except for a 5/16 inch lip around the perimeter of the cylinder. The assembly is heated from below with a bunsen burner at a rapid rate of heating to determine the approximate, or initial, smoke point which is the temperature at which smoke first appears when the assembly is viewed against a dark background. Thereafter, the smoke point is redetermined using a slow rate of heating of about 5°-10° C. per minute in the vicinity of the initial smoke point.

Lubricity of polyester filament yarn having fiber lubricants of the invention applied thereto was evaluated by applying to a scoured 150-denier polyester filament producer yarn the desired percentage of lubricant. The lubricant was applied to the yarn utilizing an Atlas Yarn Finish Applicator made by the Precision Machine Development Company in which yarn is passed at a controlled speed through a continually replenished drop of finish solution of specified strength in order to achieve a uniform wetting of the yarn. The solution is metered using a syringe pump. The yarn during treatment is passed from a feeder globule over an adjustable canter roller which functions to space the yarn filaments for passage over a drying drum utilized in conjunction with the application of heat in the application of the fiber lubricant to the yarn. The yarn finally is passed over a winding tube and is subsequently conditioned overnight under controlled conditions of temperature and humidity (65 percent relative humidity and 70° F.) before being tested. Utilizing the fiber lubricant treated yarn, the coefficient of friction (f) was determined using a Rothschild F Meter in which the yarn is passed over a 0.313 inch diameter satin chrome pin at a contact angle of 180 degrees and at a speed of 50, 100, 150, 200, 250, and, wherever possible, 300 meters per minute. Tensiometers on the Rothschild machine measure the yarn tension before and after it passes over the friction pin so as to insure uniformity of conditions. The coefficient of friction is determined directly from the instrument chart. For comparison, the polyester filament yarn is measured for lubricity prior to treatment with the fiber lubricant of the invention. Test results are shown in the following Table I.

TABLE I

| | Coefficient of Friction | |
|---|---|---|
| | Coefficient of Friction (f) 1% by weight lubricant on 150 denier polyester yarn. Speed | |
| Lubricant | 100 meters/min. | 200 meters/min. |
| Example 1 | .48 | .64 |
| Example 2 | .37 | .61 |
| Example 3 | .40 | .60 |
| Example 4 | .40 | .55 |
| No lubricant | .54 | .69 |

The following examples illustrate the various aspects of the invention but are not intended to limit it. Where not otherwise specified throughout the specification and claims, temperatures are given in degrees centigrade and parts, percentages and proportions are by weight.

EXAMPLE 1

This example illustrates the preparation of a lubricant of the invention which is the reaction product of 1,3-dihexoxy-2-propanol with 9 moles of ethylene oxide. The required alcohol intermediate, 1,3-dihexoxy-2-propanol was prepared by the following procedure. To a five liter flask equipped with a stirring device, distillation head, condenser, temperature measuring equipment, heating mantle, and protected with nitrogen, there was added 22.5 moles of 1-hexanol and 10 grams of boron trifluoride etherate. While maintaining the temperature at approximately 60° C., 18 moles of epichlorohydrin were slowly added over a period of 18.5 hours. Heating was continued for an additional four hours to insure complete reaction and the reaction mixture was allowed to stand for a period of 16 hours. Thereafter, 15 grams of sodium bicarbonate were added to destroy the boron trifluoride etherate catalyst. Thereafter, 1000 grams of the resulting crude mixture of 3-chloro-1-hydroxy-2-propanol was mixed with 1000 grams of toluene and 720 grams of a 40 percent aqueous solution of potassium hydroxide in a five liter flask equipped with a stirring device, temperature measuring equipment, heating mantle, and a Dean Stark trap-condenser assembly. The reaction mixture was then heated 11.5 hours at approximately 90°-95° C. until no further water was obtained. After filtration to remove potassium chloride and distillation to remove the toluene, the crude glycidyl ether was added over a four hour period to a round-bottom flask containing 20.3 moles of hexanol and 0.22 moles of boron trifluoride etherate, said flask being maintained at approximately 60° C. and equipped with a stirring device, distillation head, condenser, temperature measuring equipment, heating mantle, and protected with a nitrogen atmosphere. The temperature was then raised to 60° C. and maintained for approximately 3.5 hours after the addition was completed to insure complete reaction. After treatment with sodium bicarbonate, filtration to remove excess hexanol, distillation and redistillation, 617 grams of 1,3- dihexoxy-2-propanol was obtained in a yield of 52.2 percent based upon initial epichlorohydrin utilized. The composition had a boiling point of 128° C. at 0.1 millimeters of pressure.

The fiber lubricant which is a reaction product of one mole of 1,3-dihexoxy-2-propanol with 9 moles of ethylene oxide was prepared by adding 350 grams of 1,3-dihexoxy-2-propanol and 5 grams of an aqueous solution of 45 percent potassium hydroxide to an autoclave equipped with temperature, pressure, and vacuum controls. The autoclave was evacuated to less than 10 millimeters of mercury while being heated to 110° C. After most of the water had been removed, the temperature was increased to 135° C. and the autoclave was repressurized with nitrogen to 34 lbs per square inch gauge. Thereafter, 550 grams of ethylene oxide were added over a four hour period. The reaction mixture was then held at 135° C. for an additional two hours to insure complete reaction. The product was deionized to remove catalyst and the desired product was obtained having an hydroxyl number of 87 (84 theoretical) and physical characteristics as summarized in Table II and thermal characteristics as summarized in Table III.

EXAMPLE 2

This example illustrates the preparation of a lubricant of the invention by reacting one mole of 1,3-dihexoxy-2-propanol with 8.5 moles of ethylene oxide and 1.5 moles of 1,2-propylene oxide. This lubricant was made utilizing substantially the same procedure as in Example 1. The desired product obtained after deionization had a hydroxyl number of 93 (80 theoretical), physical characteristics as summarized in Table II and thermal characteristics as summarized in Table III.

EXAMPLE 3

This example illustrates the preparation of a lubricant of the invention by the reacting of one mole of 1,3-dihexoxy-2-propanol with 12 moles of ethylene oxide and 1.5 moles of 1,2-propylene oxide. Following the procedure of Example 1, the desired product was obtained after deionization with physical and thermal characteristics described respectively in Tables II and III.

TABLE II

| | Physical Characteristics of Fiber Lubricants of the Invention | | | |
|---|---|---|---|---|
| | Viscosity | | | |
| Example | Brookfield at 25° C. (cps) | Saybolt at 100° F. | Cloud Point (1% wt. sol.) (°C.) | Surface Tension (0.1% wt. sol.) dynes/cm |
| 1 | 61 | 151 | 47 | 26 |
| 2 | 50.5 | 133 | 23 | 26 |
| 3 | 81 | 217 | 54 | 27 |

TABLE III

| | Thermal Characteristics of Fiber Lubricants of the Invention | | |
|---|---|---|---|
| | Thin Film Smoke Point | Wt. % Remaining Residue at 200° C. | |
| Example | (°C.) | 30 min. | 16 hrs. |
| 1 | 154 | 14 | 1.7 |
| 2 | 176 | 1.6 | 0 |
| 3 | 176 | 1.8 | 0 |
| 4 | 168 | 65.6 | 19.9 |

EXAMPLE 4

Utilizing methods well-known to those skilled in the art, a prior art fiber lubricant was prepared, namely the laurate ester of a heteric copolymer (30 parts by weight ethylene oxide and 70 parts by weight 1,2-propylene oxide) initiated using hydroquinone of 1200 molecular weight. Thereafter, 56 parts by weight of this prior art lubricant and 44 parts by weight of the heteric copolymer of Example 2 (8.5 moles of ethylene oxide and 1.5 moles of 1,2-propylene oxide) initiated with 1,3-dihexoxy 2-propanol were blended. As shown in Table I, this blend has excellent lubricity but exhibits high residue after heating (Table III).

While this invention has been described with reference to certain specific embodiments it will be recognized by those skilled in the art that many variations are possible without departing from the spirit and scope of the invention and it will be understood that it is intended to cover all changes and modifications of the invention disclosed herein for the purposes of illustration which do not constitute departures from the spirit and scope of the invention.

The embodiments of the invention in which an exclusive property or privilege is claimed are defined as follows:

1. The process of preparing a fiber lubricating compound having the structural formula:

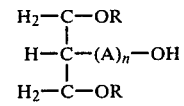

wherein R is an alkyl radical having about 3 to about 22 carbon atoms; A is a mixture of the residues of ethylene oxide and another lower alkylene oxide; n has a value to produce a molecular weight of about 300 to about 3000; and said compound is the oxyalkylation product of a glycerol-1,3-dialkylether comprising a. reacting a fatty alcohol having 3 to about 22 carbon atoms with epihalohydrin catalyzed with a Lewis acid catalyst followed by treatment with a base to form an alkoxyglycidyl ether, b. reacting said alkoxyglycidyl ether with an excess of a fatty alcohol having 3 to about 22 carbon atoms, wherein said alcohol can be the same or different than said alcohol in part (a), in the presence of a Lewis acid catalyst, c. recovering the gycerol-1,3-dialkylether intermediate produced, and d. alkoxylating said intermediate with ethylene oxide and another alkylene oxide under alkaline catalysis at a temperature of about 110° to 135° C.

2. The process of claim 1 wherein said alcohol has about 10 to about 22 carbon atoms, said epihalohydrin is epichlorohydrin, and A is derived from a heteric mixture of ethylene oxide and 1,2-propylene oxide in the respective ratio by weight of 20:80 to 90:10.

* * * * *